(12) United States Patent
Fischer et al.

(10) Patent No.: US 10,660,689 B2
(45) Date of Patent: May 26, 2020

(54) LEAKAGE PROTECTION SYSTEM, PRESSURE BALANCING SYSTEM, AND PRECIPITATOR WITH VALVE FUNCTION FOR ABLATION APPLICATIONS

(71) Applicant: AFREEZE GmbH, Innsbruck (AT)

(72) Inventors: Gerald Fischer, Voels (AT); Florian Hintringer, Ampass (AT)

(73) Assignee: AFreeze GmbH, Innsbruck (AT)

( * ) Notice: Subject to any disclaimer, the term of this patent is extended or adjusted under 35 U.S.C. 154(b) by 254 days.

(21) Appl. No.: 15/472,914

(22) Filed: Mar. 29, 2017

(65) Prior Publication Data

US 2017/0196616 A1  Jul. 13, 2017

Related U.S. Application Data

(62) Division of application No. 13/701,050, filed as application No. PCT/EP2011/058999 on May 31, 2011, now Pat. No. 9,662,162.

(Continued)

(51) Int. Cl.
*A61B 18/04* (2006.01)
*A61B 18/02* (2006.01)
(Continued)

(52) U.S. Cl.
CPC .............. *A61B 18/04* (2013.01); *A61B 18/02* (2013.01); *A61B 18/042* (2013.01); *A61B 18/1492* (2013.01); *A61B 2017/32007* (2017.08); *A61B 2017/320069* (2017.08); *A61B 2018/00642* (2013.01); *A61B 2018/00648* (2013.01); *A61B 2018/0212* (2013.01); *A61B 2018/0231* (2013.01); *A61B 2217/005* (2013.01)

(58) Field of Classification Search
CPC . A61B 17/320068; A61B 18/02; A61B 18/04; A61B 18/1492; A61B 2018/00642; A61B 2018/0212; A61B 2018/0231
See application file for complete search history.

(56) References Cited

U.S. PATENT DOCUMENTS

| | | |
|---|---|---|
| 3,859,986 A | 1/1975 | Okada et al. |
| 6,178,985 B1 | 1/2001 | Robinson |

(Continued)

FOREIGN PATENT DOCUMENTS

| | | |
|---|---|---|
| EP | 0 148 833 B1 | 4/1988 |
| EP | 0 955 012 A1 | 11/1999 |

(Continued)

*Primary Examiner* — Amanda K Hulbert
(74) *Attorney, Agent, or Firm* — Robert A. Blaha; Smith Tempel Blaha LLC

(57) ABSTRACT

An ablation device comprising an ablation applicator adapted for ablating material from an object upon delivery of an ablation medium to the ablation applicator in an ablation mode, an ablation medium supply line adapted for supplying the ablation medium to the ablation applicator in the ablation mode, an ablation medium drain line adapted for draining the ablation medium received from the ablation applicator in the ablation mode, and a closure mechanism adapted for selectively enclosing a predefined volume in a fluidic path upon operating the ablation device in a no-flow mode or upon detecting a leak in the fluidic path, the fluidic path including the ablation applicator and being defined between the ablation medium supply line and the ablation medium drain line.

20 Claims, 6 Drawing Sheets

Related U.S. Application Data

(60) Provisional application No. 61/350,177, filed on Jun. 1, 2010.

(51) Int. Cl.
*A61B 18/14* (2006.01)
*A61B 17/32* (2006.01)
*A61B 18/00* (2006.01)

(56) References Cited

U.S. PATENT DOCUMENTS

| | | |
|---|---|---|
| 6,589,234 B2 | 7/2003 | Lalonde et al. |
| 6,733,494 B2 | 5/2004 | Abboud et al. |
| 7,004,936 B2 | 2/2006 | Ryba et al. |
| 8,206,345 B2 | 6/2012 | Abboud et al. |
| 8,777,936 B2 | 7/2014 | Fischer et al. |

FOREIGN PATENT DOCUMENTS

| | | |
|---|---|---|
| EP | 1 148 833 B1 | 7/2003 |
| WO | WO1995019738 | 7/1995 |
| WO | WO1999056639 A1 | 11/1999 |
| WO | WO1999065410 A1 | 12/1999 |
| WO | WO2001070123 A1 | 9/2001 |
| WO | WO2002058576 A1 | 8/2002 |
| WO | WO2003026719 A2 | 4/2003 |
| WO | WO2004064914 A2 | 8/2004 |
| WO | WO2005038357 A2 | 4/2005 |
| WO | WO2006096272 A1 | 9/2006 |
| WO | WO2008048481 A1 | 4/2008 |

LEAKAGE PROTECTION SYSTEM, PRESSURE BALANCING SYSTEM, AND PRECIPITATOR WITH VALVE FUNCTION FOR ABLATION APPLICATIONS

CROSS-REFERENCE TO RELATED APPLICATIONS

This application is a divisional patent application of co-pending U.S. National Stage application Ser. No. 13/701,050, of the same title, filed on Feb. 6, 2013 and claims the benefit of the filing date of PCT/EP11/58999 and the filing date of U.S. Provisional Patent Application No. 61/350,177 filed Jun. 1, 2010, the disclosures of which are hereby incorporated herein by reference in their respective entirety.

TECHNICAL FIELD

The invention relates to ablation devices. Moreover, the invention relates to ablation methods. Furthermore, the invention relates to a precipitator.

BACKGROUND

Many cardiac arrhythmias can be treated by selectively blocking pathways or sources of electrical activation in the myocardial tissue by catheter ablation. The application of an ablation medium (such as radio-frequency current, extreme cold, ultra-sound, laser, etc.) triggers cell death of electrically conducting myocytes and the formation of a non-conducting lesion.

Cryosurgery is the application of extreme cold to ablate abnormal or diseased tissue. Cryosurgery works by taking advantage of the destructive force of freezing temperatures on cells. At low temperatures, ice crystals may form inside the cells, which can tear them apart. More damage may occur when blood vessels supplying the tissue freeze.

In the case of a catheter leak, there is the danger that refrigerant or another ablation medium can enter the patient's body. There is also the danger that blood or any other physiological material enters and damages the ablation system in the case of a catheter leak.

Methods for exhausting a refrigerant from a cryoablation system by a vacuum are described in U.S. Pat. No. 3,859,986 or WO 99/65410.

In cryoablation systems, extreme cold (particularly temperatures below −50° C.) are generated in the boiling chamber of a cryo-applicator (the therapeutic component in wall contact with the tissue) by vaporizing a refrigerant (Joule-Thompson effect). The pathway of refrigerant flow (supply line, throttle, boiling chamber, return or drain line) is sealed by a continuous outer jacket. When connecting a vacuum source to the return line, the refrigerant is exhausted actively from the low pressure stream of the catheter. This involves technical challenges.

In the case of leakage, blood might be sucked into the catheter. For avoiding an unacceptable loss of blood (hemorrhagic shock) proper technical measures are needed which should attenuate the consequences of a loss of blood. For this purpose, blood detection systems are described in EP 1,148,833. Due to the high risk level also two or more redundant or complementary blood detectors are used.

Methods for controlling a pressure within an ablation device are described in U.S. Pat. No. 7,004,936. Cryogenic catheters might be operated at two different flow conditions (normal flow for ablation and low flow for cryomapping). Here the use of a vacuum drain might decrease the boiling chamber pressure below the static triple point pressure of the cooling medium. Methods for maintaining a sufficiently high boiling point pressure at a low flow rate are described in U.S. Pat. No. 6,589,234.

However, conventional ablation systems may still suffer from the shortcoming that in case of a leak in an ablation catheter, it is difficult to reliably suppress blood flow into the catheter.

SUMMARY

It is an object of the invention to provide a safe and efficient ablation system.

In order to achieve the object defined above, ablation devices, ablation methods, and a precipitator according to the independent claims are provided.

According to an exemplary embodiment of a first aspect of the invention, an ablation device is provided which comprises an ablation applicator (which may comprise a catheter) adapted for ablating material (such as tissue, particularly tissue of the heart) from an object (such as a patient) upon delivery of an ablation medium (such as a refrigerant) to the ablation applicator in an ablation mode, an ablation medium supply line (such as a tubing) adapted for supplying the ablation medium to the ablation applicator in the ablation mode, an ablation medium drain line (or return line) adapted for draining (or returning) the ablation medium received from the ablation applicator in the ablation mode, and a closure mechanism adapted for selectively enclosing (or closing or sealedly separating) a predefined volume (or a predefined section) in a fluidic path upon operating the ablation device in a no-flow mode or upon detecting a leak in the fluidic path, the fluidic path including the ablation applicator and being defined between the ablation medium supply line and the ablation medium drain line.

According to another exemplary embodiment of the first aspect of the invention, an ablation method is provided, wherein the method comprises supplying an ablation medium for ablating material from an object to an ablation applicator via an ablation medium supply line in an ablation mode, draining the ablation medium received from the ablation applicator via an ablation medium drain line in the ablation mode, and selectively enclosing a predefined volume in a fluidic path upon operating the ablation device in a no-flow mode or upon detecting a leak in the fluidic path, the fluidic path including the ablation applicator and being defined between the ablation medium supply line and the ablation medium drain line.

According to an exemplary embodiment of a second aspect of the invention, an ablation device is provided which comprises a boiling chamber adapted for boiling an ablation medium for ablating material from an object, an ablation medium drain line adapted for draining the ablation medium received from the boiling chamber, a flow impedance (such as a flow resistance) arranged between the boiling chamber and the ablation medium drain line, and an ablation medium conveying unit (such as a vacuum pump) adapted for conveying (or pumping) the ablation medium to the boiling chamber, through the flow impedance and to the ablation medium drain line, wherein the ablation medium conveying unit and the flow impedance are adapted so that the ablation medium has an average flow velocity in the flow impedance (for instance a flow velocity of particles of the ablation medium averaged over a cross-section of the flow impedance) of at least about 50% of the acoustic velocity (or of the speed of sound).

According to yet another exemplary embodiment of the second aspect of the invention, an ablation method is provided which comprises conveying an ablation medium to a boiling chamber, through a flow impedance and to an ablation medium drain line, boiling the ablation medium in the boiling chamber for ablating material from an object, draining the ablation medium received from the boiling chamber in the ablation medium drain line, and conveying the ablation medium with an average flow velocity of at least about 50% of the acoustic velocity through the flow impedance.

According to an exemplary embodiment of a third aspect of the invention, a precipitator for precipitating impurities (such as liquid and/or solid components of another material than the actual ablation medium) from an ablation medium is provided, the precipitator comprising an inlet adapted for being supplied with the ablation medium comprising impurities, an outlet adapted for draining the ablation medium after at least partial removal of the impurities, an impurity removal chamber for at least partially removing the impurities from the ablation medium and being arranged between the inlet and the outlet, a floating body (such as a balloon or the like, wherein an average density of the floating body may be smaller than 0.6 g/cm$^3$, particularly smaller than 0.2 g/cm$^3$) and a sealing coupled to one another and being arranged in the impurity removal chamber, wherein the sealing is adapted for sealing the impurity removal chamber in the presence of a negative pressure in the impurity removal chamber (particularly an interior pressure in the impurity removal chamber being smaller than a pressure in an exterior surrounding thereof), wherein the floating body is adapted for being lifted within the impurity removal chamber in the presence of a liquid (or any other material having a density being larger than the density of the floating body) in the impurity removal chamber, thereby forcing the sealing to allow for a fluid communication between an interior and an exterior of the impurity removal chamber.

The term "ablation device" may particularly denote any apparatus which is adapted to ablate, deactivate, destroy or remove material, particularly tissue of a physiological object such as a human being or an animal, via the application of an ablation medium such as extreme cold provided by a cryoablation medium.

The term "ablation medium" may particularly denote a fluid, particularly a cryofluid such as $N_2O$, which is configured for providing cooling power for ablation tasks. Other possible ablation media are radio-frequency current, ultrasound, laser, etc.

The term "object" may particularly denote any object under examination, analysis or ablation and may be a human being, an animal, or any plant (any organism). More particularly, it may be an organ of such a physiological object, particularly a heart or a part thereof, for instance the isthmus. It may be a living body so that living tissue may be investigated or processed.

The term "ablation applicator" may particularly denote a member or a part of an ablation device at which the actual tissue ablation is carried out, particularly by icing tissue. The ablation applicator may be part of a catheter.

The term "ablation mode" (or flow mode or icing mode or active mode) may particularly denote an operation mode of the ablation device during which ablation medium is conveyed through the ablation device to cool the ablation applicator to actually ablate tissue from the object. During an ablation procedure, the time intervals during which the ablation mode is active may be relatively short, for instance may be below 20% of the entire operation time.

The term "no-flow mode" (or idle mode or standby mode) may particularly denote an operation mode of the ablation device during which no ablation medium is conveyed through the ablation device to cool the ablation applicator. Hence, the no-flow mode may be active during subsequent ablation mode time intervals. Also during insertion of the ablation applicator into the object, the ablation device may be in the no-flow mode.

According to a first aspect of the invention, a predefined volume around an ablation applicator such as a catheter may be selectively sealed, for instance by closing valves or any other closure mechanism, during an idle or no-load operation mode of the ablation device, or in the event of a leakage. The ablation device, particularly such a predefined volume, may be particularly prone to leakage in periods between subsequent ablation procedures, i.e. in a no-flow condition, since the vacuum within tubes for conveying refrigerant may be higher in a no-flow state as compared to an ablation state. One reason for this is that tubes may have a stronger tendency to become leaky due to kinking or the like when the vacuum inside the tubes becomes larger. By decoupling a corresponding predefined volume of the fluidic path with regard to fluid communication from the remainder of the system, problems resulting from leakage can be reduced. For instance, the system may be configured in such a manner that in a worst case scenario, leakage of body fluids such as blood of the patient into the system may be limited to an amount which is not medically dangerous for the patient. Such a limitation may be guaranteed by adjusting the pressure conditions within the system so that in equilibrium after leakage, the amount of blood flown into the system always remains well below a clinically tolerable level. Closing the predefined volume may maintain a moderate vacuum in its interior. In the event of a leakage, blood or any other medium surrounding the predefined volume may flow into the predefined volume. However, the defined dimension of this volume and the pressure conditions may be adjusted to only allow a predetermined amount of such a medium to flow into it, since the medium will reduce the vacuum therein. Thus, a proper design of the pressure conditions in the ablation device and of the dimension of the predefined volume allows limiting dangers connected with a leakage.

According to a second aspect of the invention, a flow impedance may be selectively introduced into the ablation device, more precisely between a boiling chamber of the ablation device and an ablation medium drain line. Such a defined flow impedance, particularly a narrow section or bottleneck in the ablation medium flow path, may allow to make use of the so called chocked flow effect. This may ensure that deviations in a sucking pressure do not have a negative impact on the pressure conditions in the boiling chamber, thereby a pressure balance is obtained. In this context, it may be advantageous that the velocity of the ablation medium when passing the flow impedance may be close to the acoustic velocity.

According to a third aspect of the invention, a precipitator is provided which can be integrated in a safety system for preventing undesired effects in case of the leakage of the ablation applicator when implanted in a patient. Such a precipitator may include a floating body coupled to a sealing element and being adapted to be uplifted in the presence of a leak due to which the precipitator is filled at least partially with blood or the like. In this case, the floating body may be uplifted, thereby disabling the sealing effect of the sealing element so that a negative pressure in the precipitator and adjacent sections may be reduced. Additionally or alternatively, the uplifting of the floating body can be also used for triggering an alarm or the like.

In the following, further exemplary embodiment of the ablation devices will be explained. However, these embodiments also apply to the methods and to the precipitator.

In an embodiment, the closure mechanism may be a valve-controlled closure mechanism. Particularly the combination of two individually switchable valves delimiting the predefined volume when both being closed may serve as a safety mechanism with regard to leakage and may be implementable with reasonable effort.

More particularly, the closure mechanism may comprise a supply valve arranged in the ablation medium supply line. Hence, the supply valve be arranged upstream (in an ablation medium transport direction) of the ablation applicator, i.e. the actual catheter.

In an embodiment, the supply valve may be adapted for being opened for supplying the ablation medium to the ablation applicator and for being closed for enclosing the predefined volume. Switching of the supply valve may be performed manually by a user or controlled by the system, for instance under control of a control unit such as a central processing unit. Switching the supply valve on may be triggered by a start command of the user desiring to start an ablation procedure or desiring to start a new flow phase (for instance after a previous no-flow phase). Switching the supply valve off may be triggered by a transition from a flow phase to a no-flow phase. Switching the supply valve off may also be triggered by the event of detecting a leakage for terminating the ablation procedure and for ensuring that leakage does not have an impact on the entire ablation device, but only to a very small volume thereof.

In an embodiment, the closure mechanism may comprise a drain valve arranged in the ablation medium drain line. Hence, the drain valve be arranged downstream (in an ablation medium transport direction) of the ablation applicator, i.e. the actual catheter.

The drain valve may be adapted for being opened for draining the ablation medium and for being closed for enclosing the predefined volume. Operation of the drain valve may be performed manually by a user or controlled by the system, for instance under control of a control unit such as a central processing unit. This control unit may be the same or another control unit which controls the supply valve. Switching the drain valve on may be triggered by a start command of the user desiring to start an ablation procedure. Switching the drain valve off may be triggered by a transition from a flow phase to a no-flow phase. Switching the drain valve off may also be triggered by the event of detecting a leakage for terminating the ablation procedure and for ensuring that leakage does not have an impact on the entire ablation device, but only to a very small volume thereof.

In an embodiment, the supply valve and/or the drain valve may be adapted as a normally-closed valve. The term "normally-closed valve" may particularly denote a valve which is closed in a default mode (i.e. in the absence of an external actuation of the device), and which has to be actively controlled for being opened. Such an operation may be very safe, since this may prevent that in case of a malfunction of one of the valves or in case of an electric shortage, the valves remain open and unintentionally continue supply of ablation medium.

Alternatively, the supply valve and/or the drain valve may be adapted as a normally-opened valve. The term "normally-opened valve" may particularly denote a valve which is opened in a default mode (i.e. in the absence of an external actuation of the device), and which has to be actively controlled for being closed. Using one or more normally-opened valves may be advantageous from the point of view of the cooling losses caused by a valve. A normally-opened valve has a lower power consumption and causes therefore lower cooling losses during an ablation procedure as compared to a normally-closed valve. Hence, if the reduction of cooling losses are of importance for a certain application, the use of a normally-opened valve for the supply valve and/or the drain valve may be advantageous.

In an embodiment, the supply valve and/or the drain valve may be a magnetic valve. Switching a magnetic valve is fast, easy and reliable. For instance, a magnetic valve with a stainless steel housing may be used which can be operated with low power consumption, thereby causing only low cooling losses.

In an embodiment, the closure mechanism may be adapted for closing the drain valve subsequently to closing the supply valve upon transiting from an ablation mode (or a flow mode) to a no-flow mode. It may be appropriate to first switch the drain valve, followed by a switching of the supply valve. Switching the drain valve can be detected by a sensor arranged close or next to the drain valve. This detection may trigger switching the supply valve. The latter operation may be safe, since this may prevent that for instance due to a malfunction of the drain valve, the supply of ablation medium is still continued.

In another embodiment, both the supply valve and the drain valve may be switched simultaneously which may simplify control operation.

In an embodiment, the closure mechanism may be adapted for opening the drain valve prior to opening the supply valve upon transiting from a no-flow mode to an ablation mode. This may allow an ablation medium conveying unit such as vacuum pump to suck off ablation medium or impurities from the ablation medium drain line before supply of fresh ablation medium.

In an embodiment, the ablation device may comprise a sensor (such as a pressure sensor) which may be arranged in the ablation medium drain line upstream the drain valve, for instance directly adjacent or close to the drain valve. Such a sensor may detect opening of the drain valve which is detectable by a sudden pressure change or by a certain pressure characteristic.

The sensor may be adapted for sensing closure of the supply valve and for triggering closing of the drain valve with a predefined time delay in between. Hence, the sensor may trigger switching of the supply valve after a predefined time delay (for instance one second). In this time interval, the line between the valves may be evacuated and hence cleaned by the ablation medium conveying unit.

The sensor may be adapted for sensing a leakage and, upon detecting the leakage, for closing the supply valve. Such a leakage may introduce material into the ablation medium lines, and this has an impact on the pressure conditions within the ablation medium lines as well. A characteristic change of the pressure conditions may be detected by the sensor and may serve as a trigger for switching the above mentioned valves for reducing a negative impact of the leakage on the ablation device.

In an embodiment, the ablation device may be adapted so that, upon closing the predefined volume, a pressure difference between a pressure in the object and a pressure in the predefined volume is in a range between about +0.05 bar and about +0.6 bar, particularly in a range between about +0.25 bar and about +0.5 bar (the sign "+" shall indicate that the pressure inside the tubing delimiting the predefined volume and the fluidic path is smaller than the pressure in the surrounding, for instance in the blood or in tissue of the object such as a patient). In an embodiment, this "exhaustion pressure", i.e. the difference of pressure between a medium surrounding the ablation device (such as blood or air) and a vacuum or negative pressure in the ablation medium drain line, which is defined to be positive for a vacuum or negative pressure condition, may be in a range between about 0.05 bar and about 0.6 bar, particularly may be in a range between about 0.25 bar and about 0.5 bar. The upper limit of these ranges ensures that a surrounding medium such as blood flowing into the ablation device in the case of a leakage does not become too large. Due to the negative pressure within the lines, surrounding medium may be sucked into the leaky lines until equilibrium is achieved. Thus, the smaller the pressure difference, the smaller is the amount of material sucked into the lines. However, some material flow into the lines is desired for allowing for an early detection of the leak. Hence, the lower limit of these ranges allows some amount of the surrounding medium such as blood to flow into the ablation device in case of leakage, thereby allowing for a sufficiently early leak detection before icing and other undesired effects occur.

In an embodiment, the predefined volume, i.e. the technically realized volume between the valves, may be chosen to be smaller than about 200 ml, particularly smaller than about 120 ml. In an embodiment, the predefined volume may be in a range between 20 ml and 200 ml, particularly in a range between 60 ml and 120 ml. This ensures that the loss of blood leaking into the lines is not dangerous for the patient. On the other hand, this insures that the impact of leaking material on the ablation device is sufficiently small.

In an embodiment, the ablation device may comprise an impurity filter adapted for filtering impurities from the ablation medium. Blood, dirt, dust or the like can be removed from the fluidic path by the impurity filter.

In an embodiment, the impurity filter may be arranged within the predefined volume downstream the ablation applicator (although other positions are possible). It may be advantageous to arrange the impurity filter between the supply valve and the drain valve to avoid any undesired impact of the impurities on the drain valve.

In an embodiment, the ablation device may comprise a precipitator adapted for precipitating impurities from the ablation medium. Such a precipitator may be a container having an inlet and an outlet (which may be located in an upper or even a top portion the container), wherein the expanded gaseous ablation medium can be supplied to the inlet and may be drained via the outlet, promoted by a pumping pressure. Liquid and solid components of the medium passing the precipitator may be accumulated in a bottom portion the container.

In an embodiment, the precipitator may be arranged within the predefined volume downstream the ablation applicator. It may be advantageous to arrange the precipitator between the supply valve and the drain valve to avoid any undesired impact of impurities on the drain valve.

In a particularly preferred embodiment, the precipitator may comprise the above mentioned floating body and sealing element which allows to simultaneously use the precipitator as a cleaning feature, a pressure controlled valve and/or a leakage alarm detection system.

The ablation device may comprise an ablation medium conveying unit (such as a vacuum pump) adapted for conveying the ablation medium. The ablation medium conveying unit may be arranged downstream of the ablation medium drain line (although other positions are possible).

The ablation medium conveying unit may convey the ablation medium through the ablation medium line and may maintain a negative pressure in the ablation medium line. The ablation medium conveying unit may be arranged downstream of and outside of the predefined volume.

The ablation device may further comprise drain container arranged downstream the drain valve and (with regard to fluid flow) in parallel to the ablation medium conveying unit. Such a container may be basically at the same pressure as a vacuum pump of the system, and may serve as a buffer or pressure smoothing feature for smoothing pressure shocks. The drain container may also accommodate material pumped through the ablation medium lines.

The drain valve may be arranged so that, in its closed state, the predefined volume is decoupled from the ablation medium conveying unit. Hence, the drain valve may define the downstream end of the predefined volume. Accordingly, the supply valve may form the upstream end of the defined volume.

The ablation applicator may comprise a boiling chamber adapted for boiling the ablation medium for ablating material from the object. Hence, the boiling chamber may be the actual portion of the ablation device in which the ablation medium, such as a cryofluid, is expanded and therefore provides cooling power due to the Joule-Thompson effect.

In an embodiment, a flow impedance may be arranged between the boiling chamber and the ablation medium drain line. Such a flow impedance, for instance a narrow portion or a bottleneck in the fluidic path, may make use of the choked flow effect and may therefore prevent an undesired pressure coupling between boiling chamber and drain line. A speed of the ablation medium passing through the flow impedance may be at least 50%, particularly at least 90%, of the acoustic velocity. This speed may denote a speed of different fractions of the ablation medium, averaged over the cross-section of the flow impedance. Due to friction effects and the like, the speed of fractions of the ablation medium close to the walls of the flow impedance may be smaller than the speed of fractions of the ablation medium in a central portion of the flow impedance.

More particularly, the ablation medium conveying unit and the flow impedance may be adapted so that the ablation medium has an average flow velocity in the flow impedance of at least about 50% of the acoustic velocity. Thus, the speed may depend on the pumping strength of the ablation medium conveying unit as well on the geometry of the flow impedance.

In an embodiment, the flow impedance may be adapted as a constricted opening between the boiling chamber and a suction chamber of the ablation medium drain line via which suction chamber boiled ablation medium is sucked off. For instance, each of the boiling chamber, the suction chamber, and the ablation medium drain line may have a tubular shape. A cross-section of the tube forming the flow impedance may be smaller than a cross-section of the tube forming the boiling chamber which may, in turn, be smaller than a cross-section of the tube forming the suction chamber. Such a geometry is a simple way to promote the desired decoupling between boiling chamber and suction chamber.

In an embodiment, the absolute pressure in the suction chamber may be smaller than a pressure in the flow impedance. A pressure in the boiling chamber may be larger than a pressure in the flow impedance. Such pressure conditions may ensure that the flow impedance may fulfill the desired effect.

In an embodiment, the ablation device may optionally comprise one or more blood sensors. Such (a) blood sensor(s) may be arranged within the predefined volume, particularly within the catheter, and may be adapted for sensing the presence of blood due to a leakage. Additionally or alternatively, one or more blood sensors may also be arranged at any other position in the ablation device, for instance in a handle and/or in a console of the ablation device. There are different alternative possibilities of detecting a leakage, for instance using an optical sensor, a chemical sensor, the precipitator having a floating body, an optical inspection of the catheter showing blood leakage, etc. Upon detecting a leakage, the predefined volume may be quickly closed, even during an ablation mode. Additionally or alternatively, an alarm may be triggered upon detecting a leak. Upon detecting a leakage, it is possible to first close the supply valve and then the drain valve, as a safety feature.

The ablation device may comprise a bypass line having a bypass valve. The bypass line may connect a container containing the ablation medium with the ablation medium drain line bypassing the predefined volume. By such a bypass line being selectively openable or closable by a bypass valve arranged in the bypass line, the termination of an ablation procedure may be simplified, since ablation medium may be drained directly without being guided through the ablation applicator, if desired.

The bypass valve may be a normally-open valve being closable during ablation. This may be advantageous for keeping the electric power consumption small, since for many applications, the no-flow condition (in which the bypass valve should be open) is active for a significantly longer time than the flow (or ablation) condition (in which the bypass valve should be closed).

The ablation device may comprise a handle for handling the ablation applicator by a hand of a human user. The handle may be at least partially made of an optically transparent material (i.e. material being optically transparent for at least a part of wavelengths between 400 nm and 800 nm) so that blood entering the handle becomes visible to the eyes of the user. Hence, a handle of the catheter may be made in a transparent or translucent fashion, by using a transparent or translucent material for the components defining the cover of the handle. Thus, blood may become already visible when entering the catheter handle. In other words a smaller amount of blood sucked from the patient's body becomes visible.

The ablation may be performed in a catheter laboratory comprising a table adapted for receiving a body of a patient thereon during ablation. The table may be located above a low pressure path of the ablation device. The term "above" may refer to a direction of the gravitation force. Particularly, a lying surface of the table may be located not more than 140 cm, particularly not more than 80 cm, more particularly not more than 60 cm, above one component (particularly above the lowest one of the components) in the low pressure path of the ablation device between the catheter and the drain valve. In other words, the physical effect of the described feature is defined by the lowest position along a path from the catheter to the vacuum valve. The low pressure path may particularly include a fluidic path downstream the ablation applicator (particular downstream the boiling chamber), more particularly downstream a precipitator. Thus, the low pressure part may be positioned below the table to not disturb a physician during the ablation procedure. However, the low pressure part may be positioned not too far below the table so that an additional hydrostatic pressure difference does not become too large which could deteriorate the device performance and might increase the volume of blood entering the fluidic path in case of a leakage.

In an embodiment, the ablation device comprises a controllable adjustment device (for instance configured as a selective pressure reducer) adapted for adjusting at least one of a pressure value and/or a flow rate (flowing mass of ablation medium per time interval) of ablation medium flowing in the ablation medium supply line towards the ablation applicator. This may allow to fine-tune the conditions according to which the ablation medium impacts the ablation applicator. This adjustment device may also act as a safety mechanism since it may allow to rapidly reduce the pressure in case of an emergency scenario.

In an embodiment, the adjustment device may be adapted for being controllable for performing the adjusting based on a sensor signal of a sensor arranged in the supply line of the ablation device. Particularly, such a sensor may form part of the closure mechanism and/or may be arranged upstream of the ablation applicator. It is possible that the sensor value providing the control signal for the adjustment device defines a set value for the output controlled by the adjustment device. For instance, a set-point for flow and/or pressure can be set to zero (or any other predetermined reference value) in an intermediate period between adjacent ablation cycles, thereby improving safety of operation.

In the following, further exemplary embodiment of the precipitator will be explained. However, these embodiments also apply to the ablation devices and to the methods.

The precipitator may comprise a stud coupling the floating body and the sealing. The stud may rigidly couple the floating body to the sealing, thereby ensuring a reliable force coupling between the floating body and the sealing element. Hence, the sealing element may selectively enable or disable the sealing effect, whereas the floating body is subject to an uplift due to fluid entering in case of a leakage.

The precipitator may comprise a biasing element exerting a biasing force on the floating body and the sealing. Hence, this biasing force adjusts a sealing strength. The biasing element may particularly comprise a spring such as a screw spring. Such a biasing element may allow to properly adjust the interaction between the sealing influence of a negative pressure within the line and the non-sealing influence of a leakage. Thus, properly configuring the biasing element allows tuning the sensitivity of the system.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DETAILED DESCRIPTION

Figure 1:
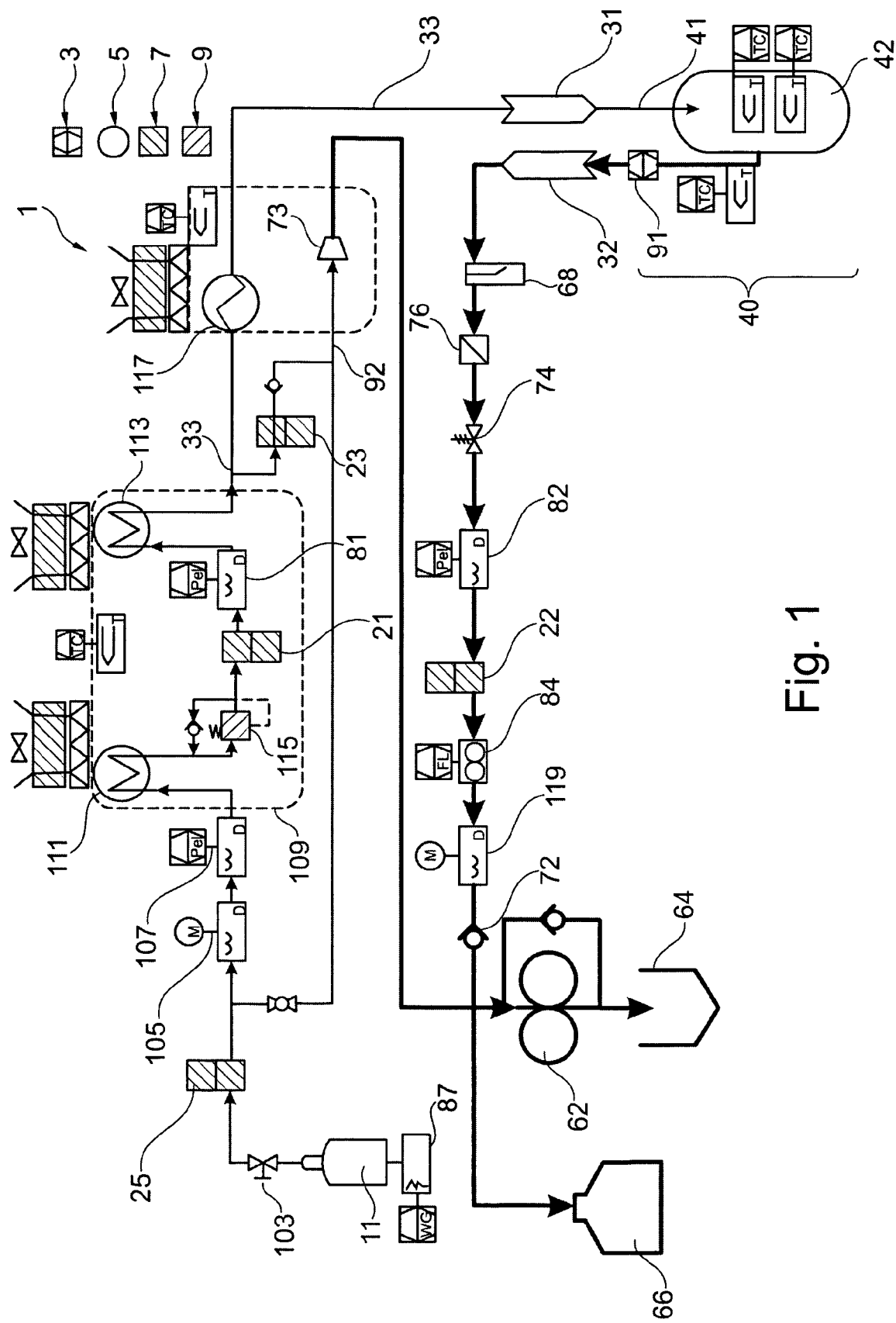
FIG. 1 illustrates an ablation device according to an exemplary embodiment of the invention.

The illustration in the drawing is schematically. In different drawings, similar or identical elements are provided with the same reference signs.

Before describing exemplary embodiments of the invention in further detail, some basic considerations of the present inventors regarding operation modes of ablation devices will be explained. Based on these considerations, exemplary embodiments of the invention have been developed.

For the time preceding or following an actual ablation procedure, no refrigerant flow occurs in an ablation device. A corresponding operation mode may be denoted as "no-flow condition". Thus, without suitable technical measures, the vacuum source would deliver its maximal pressure difference to air (typically more than 0.7 bar exhaustion pressure, $\Delta p$) as the vacuum pumps work at (almost) zero flow. During a typical catheter intervention, a cryoablation device may be in the no-flow condition for by far the major part of the time.

Throughout this application, the term "exhaustion pressure" is used for the difference of pressure, $\Delta p$, between the surrounding medium (blood or air) and a vacuum in an ablation medium line. It is defined to be positive for a vacuum condition. Absolute pressures are marked by p.

A pressure difference between an interior and an exterior of ablation medium lines leads to mechanical forces onto the low pressure stream of the cryoablation device. These forces require proper physical dimensions of all components (for example wall thickness for tubing) and, in particular, it increases the likelihood to damage the components during the intervention by kinking and similar effects.

Another operation mode of an ablation device may be denoted as "flow condition" (or "ablation condition"). During freezing (continuous refrigerant flow), proper technical measures would be desirable for controlling or limiting the exhaustion pressure $\Delta p$. If the absolute pressure p in the boiling chamber drops below the triple point pressure of the refrigerant, a transition from the liquid phase to the solid phase starts (for example if carbon dioxide is the cooling medium this condition is termed dry ice). This reduces the thermal coupling of the refrigerant with outer jacket of the boiling chamber and, thus, also with the tissue which should be treated. Furthermore, the solid ice particles might lead also to a (partial or complete) clogging in the low pressure stream of the catheter. Apart from flow rate, the absolute pressure p in the boiling chamber is also influenced by other physical parameters such as the absolute pressure in the atmosphere or a change of the back flow resistance for instance due to squeezing of the tubing.

In an embodiment of the invention and in view of the foregoing, a low pressure exhaustion system for cryoablation is provided. Such a system may be configured for cryoablation (therapeutic destruction of tissue by the application of extreme cold). A low pressure exhaustion system or method (moderate vacuum) exhausts the used, gaseous refrigerant from a cryoablation system. This ensures that in the case of a catheter leak no refrigerant can enter the patient's body.

The described exhaustion system includes mechanisms which limit the exhaustion pressure for zero flow and flow conditions to a moderate level. These methods do not necessarily need the implementation of elaborated controlling mechanisms. Furthermore, holding the exhaustion pressure at a moderate level for no-flow and flow condition, the risk of a hemorrhagic shock is reduced. Moreover, the described effects for no flow condition and flow condition may also serve as a safety mechanism in the event of an electrical power outage.

A cryo-ablation system may comprise a cryo-console housing the refrigerant tank, instrumentation and control, and a cryo-ablation catheter connected to the console by a connection line and cables.

In the following, referring to FIG. 1, an ablation device 1 according to an exemplary embodiment of the invention will be described.

Generally, symbol 3 denotes sensors, symbol 5 denotes displays, symbol 7 denotes actuators, and symbol 9 denotes adjustment elements.

Ablation device 1 comprises an ablation applicator 40 in the form of a cryocatheter (or simply a catheter) adapted for ablating material from tissue of a patient upon delivery of an ablation medium such as a cryofluid to the ablation applicator 40 in an ablation mode (i.e. an operation mode of the ablation device 1 in which tissue is actually ablated by freezing).

Ablation device 1 further comprises an ablation medium supply line 31, 33 adapted for supplying the ablation medium to the ablation applicator 40 in the ablation mode, and an ablation medium drain line 32 adapted for draining the ablation medium received from the ablation applicator 40 in the ablation mode.

A closure mechanism formed by valves 21, 22 and a pressure sensor 82 (capable of detecting a pressure, for instance in bar) is provided which operates as a safety mechanism to prevent damage in case of a leakage and which is adapted for selectively enclosing a predefined volume in a fluidic path of ablation medium supply line 31, 33 and ablation medium drain line 32. Closing the predefined volume, which can otherwise be in fluid communication with the other components of the ablation device 1, may be triggered by changing an operation mode to a no-flow mode, i.e. upon operating the ablation device 1 in a no-flow mode.

Closing the predefined volume may be triggered, additionally or alternatively, by the event of a leakage in the ablation device 1 (for instance directly detected in the fluidic path by a blood sensor or the like, or indirectly detected by recognizing that a system parameter is indicative of the presence of a leakage).

The closure mechanism comprises supply valve 21 arranged in the ablation medium supply line 33 upstream of the ablation applicator 40. The supply valve 21 is adapted for being opened for supplying the ablation medium from supply tank or container 11 to the ablation applicator 40 and for being closed for contributing to the enclosing of the predefined volume. A refrigerant, as an example for an ablation medium, is stored in supply tank 11. A bottle valve 103 and a main valve 25 allow for selectively enabling or disabling supply of refrigerant. Reference numeral 105 denotes a bottle pressure manometer, and reference numeral 107 denotes a bottle pressure sensor. A weighing machine 87 may be functionally coupled to supply tank 11 for detecting in due time when an amount of refrigerant stored in supply tank 11 falls below a critical level.

The closure mechanism additionally comprises drain valve 22 arranged in the ablation medium drain line 32 downstream of the ablation applicator 40. The drain valve 22 is adapted for being opened for draining the ablation medium and for being closed for contributing to the enclosing of the predefined volume. A vacuum manometer arranged downstream the drain valve 22 is denoted with reference numeral 119.

The supply valve 21 and the drain valve 22 are both adapted as normally-closed magnetic valves, which are normally (i.e. in the absence of an actuation signal) in a closed state and are only brought to the opened state upon applying a dedicated actuation signal. The closure mechanism is adapted for closing the drain valve 22 subsequently and with a defined delay to the closing of the supply valve 21 upon transiting from a flow mode to a no-flow mode. The closure mechanism is further adapted for opening the drain valve 22 prior to opening of the supply valve 21 upon transiting from a no-flow mode to a flow mode.

Pressure sensor 82 is arranged in the ablation medium drain line 32 upstream (related to a flowing direction of ablation medium) the drain valve 22 and is adapted for sensing closure of the drain valve 22 and for triggering opening of the supply valve 21 with a predefined time delay. The pressure sensor 82 is adapted for sensing a leakage (indicated by a pattern of the flow which is characteristically modified by a leak) and, upon detecting the leakage, for closing the supply valve 21.

The ablation device 1 comprises an impurity filter 76 arranged within the predefined volume downstream the ablation applicator 40 and is adapted for filtering impurities such as blood, dirt or dust from the ablation medium.

Figure 6:
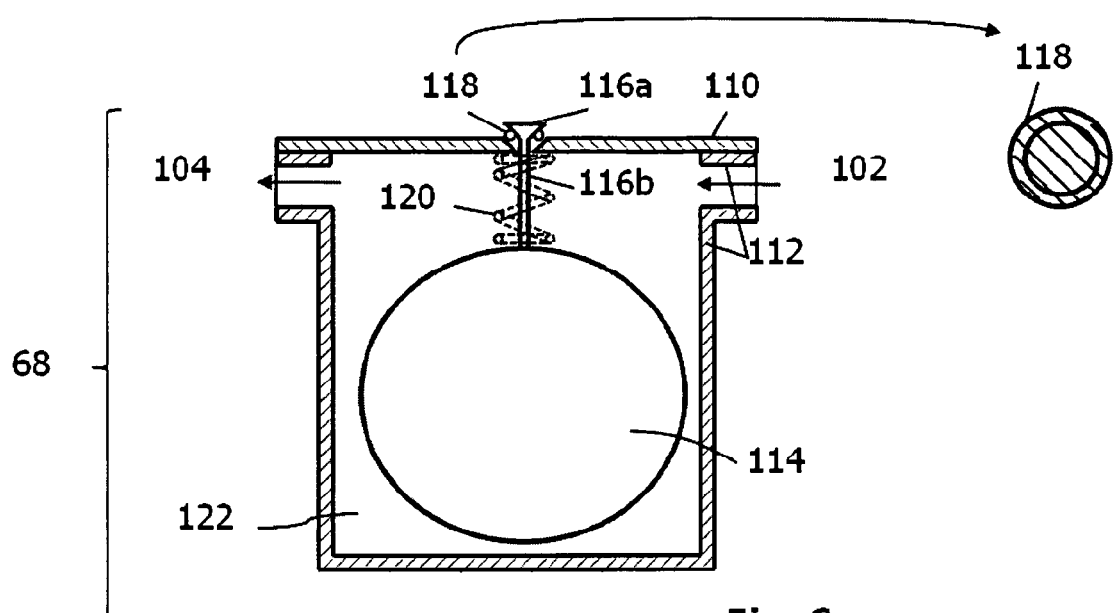
FIG. 6 illustrates a precipitator of an ablation device according to an exemplary embodiment of the invention.

The ablation device 1 additionally comprises a precipitator 68 arranged within the predefined volume downstream the ablation applicator 40 and is adapted for precipitating impurities from the ablation medium. Preferably but not necessarily, such a precipitator 68 is configured as shown in FIG. 6.

The ablation device 1 comprises an ablation medium conveying unit 62 (such as a vacuum pump) adapted for conveying the ablation medium through the fluidic path and being arranged downstream of the ablation medium drain line 32. A drain container 66 is arranged downstream (related to a flowing direction of ablation medium) the drain valve 22 and in parallel to the ablation medium conveying unit 62. The drain valve 22 is arranged so that, in its closed state, the predefined volume is decoupled from the ablation medium conveying unit 62.

The ablation device 1 comprises a bypass line 92 having a bypass valve 23 which is a normally-open valve. The bypass line 92 connects container 11 containing the ablation medium with the ablation medium drain line 32 bypassing the predefined volume, i.e. preventing directing the ablation medium through the ablation applicator 40.

A conditioner (precooling and pressure reduction of the ablation medium) 109 allows conditioning the ablation device 1 and includes, inter alia, a first heat exchanger 111 and a second heat exchanger 113. Furthermore, conditioner 109 comprises a pressure reducer 115 and a high pressure sensor 81.

Moreover, a third heat exchanger 117 (a second precooling unit) is connected in parallel to a throttle 73 and is arranged downstream the conditioner 109.

In the following, operation of the ablation device 1 will be explained.

Freezing is started by opening the supply valve or cooling valve 21. A dip pipe is used for guiding the refrigerant in its liquid phase through the high pressure stream connection line 31 to the ablation applicator or catheter 40. Passing a throttle, a pressure drop occurs and the refrigerant vaporizes in boiling chamber 42. The wasted, gaseous refrigerant is guided through the ablation medium drain line (or low pressure connection line) 32 and the opened drain valve or vacuum valve 22 to vacuum pump 62 which actively blows it into the air or into the vacuum system of a hospital 64.

Upon stopping freezing, the cooling valve 21 is first closed and with a short temporal delay, bypass valve 23 is opened, guiding the remaining refrigerant in the high pressure stream via a throttle 73 directly to the vacuum pump 62 (fast turn off of freezing). A properly dimensioned vacuum chamber 66 ensures that the transient peak of refrigerant flow does not create an over pressure with respect to the atmosphere at the connection of the vacuum pump 62 with the low pressure return of the cryoablation system.

A check valve 72 avoids that the transient bypass flow streams back into the catheter 40. Once all refrigerant has been removed from the high pressure line, the vacuum source (formed by vacuum pump 62 and/or vacuum system of hospital 64) again evacuates the vacuum chamber 66 for providing a high exhaustion pressure $\Delta p$ (typically more than 0.7 bar). The vacuum pump 62 may be controlled in order to provide a defined low pressure level. Alternatively it may be operated without control loop feedback providing a sufficiently large exhaustion pressure. In another embodiment, the vacuum system of hospital 64 is the only vacuum source.

For limiting the amount of sucked blood in the case that a leakage occurs in the time span the time preceding or following an ablation (no flow condition) the following measures may be taken:

When connecting the catheter 40 to control instrumentation and after each freeze, the exhaustion pressure $\Delta p$ in the vacuum chamber 66 will rise from a low value to a high value as the evacuation of the vacuum chamber 66 (and the low pressure lines 32) progresses. The cross sections of the low pressure stream are dimensioned sufficiently large to transport the nominal refrigerant flow of the ablation device 1. Thus, for the considered no-flow condition the pressure in the boiling chamber 42 approximately equals the pressure in the vacuum chamber 66 and in the entire low pressure pathway.

Low pressure sensor 82 monitors this low pressure. In the shown embodiment, pressure sensor 82 is arranged directly adjacent to valve 22. Alternatively, sensor 82 may be arranged at another appropriate position such as between reference numerals 32 and 68. Once a preselected exhaustion pressure $\Delta p_P$ is obtained, the vacuum valve 22 may be closed. The preselected exhaustion pressure $\Delta p_P$ may be selected just large enough that leakages can be properly detected. This pressure may be preselected to be in the range of 0.05 bar and 0.6 bar and more particularly between 0.25 bar and 0.5 bar.

Once the catheter 40 and the connection lines 32, 31 are completely separated from the vacuum pump 62, the pressure in the part left from the drain valve 22 (vacuum chamber pressure $\Delta p_V$) and right from the drain valve 22 (boiling chamber pressure $\Delta p_B$) are independent from each other. The vacuum chamber pressure $\Delta p_V$ takes a high value with proceeding evacuation. In contrast (under the idealized assumption of perfect sealing) the boiling chamber pressure $\Delta p_B$ in the catheter 40 will remain constant and equal to the preselected value chamber pressure $\Delta p_P$. As the lumina at the boiling chamber pressure $\Delta p_B$ (catheter 40 and connection lines) are not connected to the vacuum pump 62, they may be termed unconnected lumina. Real sealing cannot avoid small remaining leakage which leads to a small decrease of the boiling chamber pressure $\Delta p_B$ (typically less than 2 mbar/second). This almost constant pressure difference to the ambient is monitored by sensor 82. In case of a leakage due to damage (for example a mechanical injury in the outer jacket of the catheter 40) the surrounding medium (for example air, blood or a saline solution) will be sucked into the unconnected lumina. Thus, the pressure $\Delta p_B$ quickly drops to almost zero (typically more than 6 mbar/second). Using proper threshold values for the boiling chamber exhaustion pressure $\Delta p_B$ and its time derivatives, a safety system can detect the error condition and disable the start of a freeze and activate adequate warnings or error messages.

During a catheter intervention the catheter 40 may be disconnected from the connection line 32 or the connection line 32 may be disconnected from the ablation device 1 during the no flow phase. This corresponds to a leakage with an extremely fast drop of the boiling chamber pressure (typically more than 100 mbar/second). It may be desirable that this operator enforced disconnection (which does not go along with damage of the components) is distinguished from a harm of the ablation system. Thus another threshold might be used in the safety system for suppressing an alarm or warning in the case of an intended disconnection of a component from the ablation system. However, a corresponding message may be displayed by the system in the described scenario.

Precipitator (or liquid separator) 68 and impurity filter (or particle filter) 76 may be included for protecting the instrumentation in the low pressure stream for being polluted by blood or dust sucked from the environment.

Figure 1A:
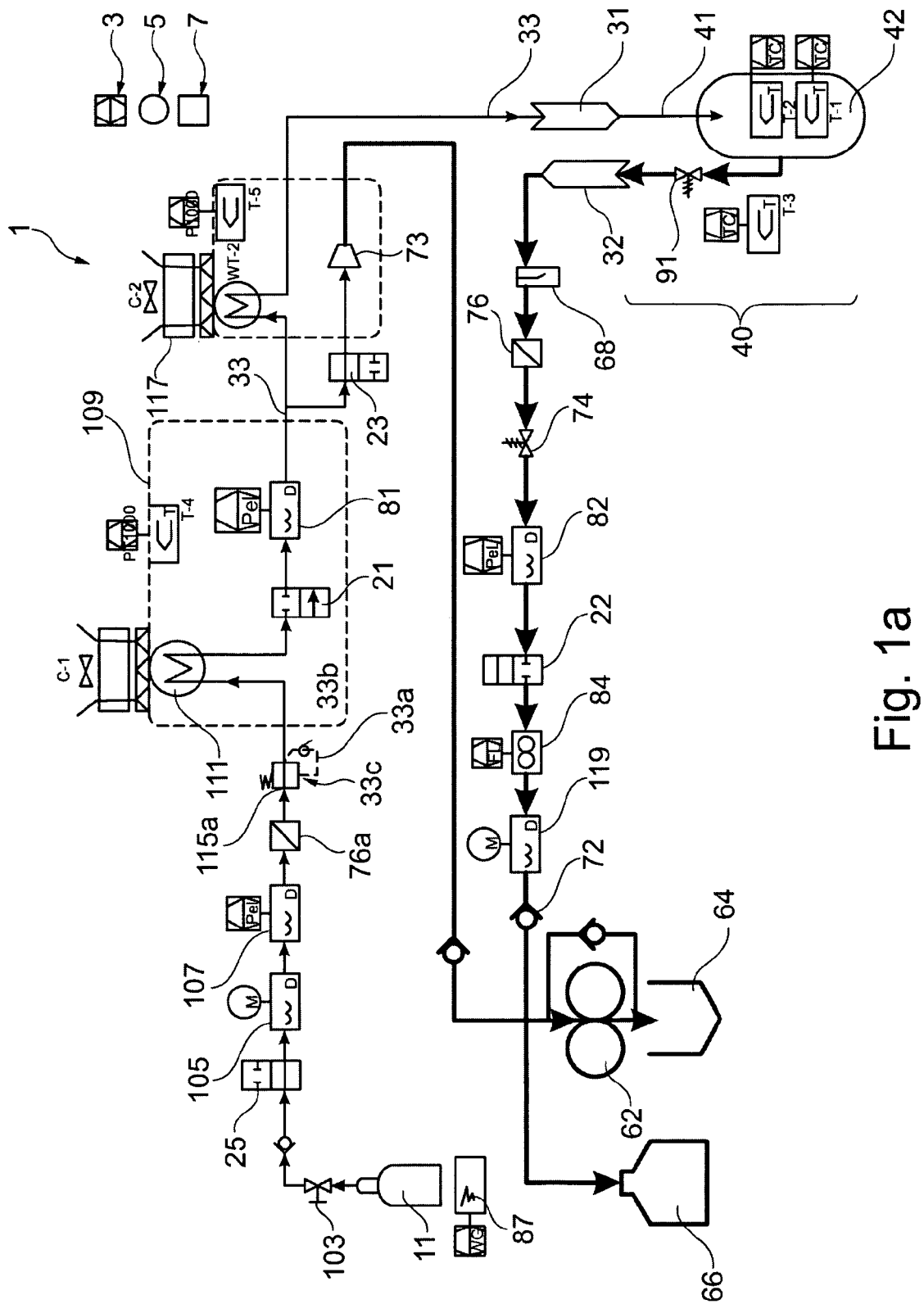
FIG. 1a illustrates an ablation device according to another exemplary embodiment of the invention.

Referring now to FIG. 1*a*, an ablation device 1 according to another embodiment is shown. Here the mechanical pressure reducer 115 of FIG. 1 has been replaced by an electronically controllable adjustment device 115*a*, which can be used to adjust the high pressure and/or the flow rate to the catheter 40. This adjustment device 115*a* for example may contain a moveable plunger within a narrow nozzle (not shown). A magnetic coil can be used for moving the plunger forward and backward within the nozzle, modulating the flow resistance in a desired fashion. An electronically adjustable pressure drop and thus, a modulation of the flow rate become possible. Multiple-purpose members which can be implemented as an adjustment device 115*a* according to an embodiment of the invention are, as such, manufactured and commercially available for example by Bronkhorst High-Tech B.V. (Netherlands) and available as mass flow controllers or pressure controllers. In the shown embodiment the adjustment device (or adjustable pressure reducer) 115*a* has been placed outside of the precooling unit 109 in a case in which is not designed for operating at low temperatures. However, if an adjustment device 115*a* is implemented which is designed for operating at low temperatures, such an adjustment device 115*a* may also be arranged within this precooling unit.

The electronically adjustable device 115*a* may contribute to keep the flow rate within tighter limits with varying ambient conditions (such as temperature) and refrigerant filling level compared to a pressure reducer with a rigidly fixed output pressure. This may contribute also to keeping the pressure levels in the low pressure exhaustion system within predefined levels and contributes thus to the stability and safety of the system. In one embodiment the adjustment device 115*a* may be controlled by the output signal of the flow sensor 82 and in another embodiment by the output signal of the pressure sensor 81. In yet another preferred embodiment the flow rate measured by flow sensor 82 defines a set value for the pressure output controlled by the adjustment device 115*a* (cascade control of flow and pressure).

Here, the set-point for flow and/or pressure can be set to zero (or a small value) in the waiting period between two freezes which provides an additional safety feature. If the supply valve 21 opens due to failure the adjustable device 115*a* may then be in the configuration in which it displays its highest flow resistance and limits thus pressure and flow to a small value. Here, the safety of the system can be further increased by opening the by-pass valve 23 in the stand-by mode between two freeze cycles. In this case the small residual flow obtained by a failure of valve 21 is guided almost completely into the low pressure drain. Additionally also supply valve 25 may be closed for stopping refrigerant supply in the case of failure of valve 21. Similarly, for a failure in which supply valve 21 does not close at the end of the freezing cycle, the electronically adjustable device 115*a* and/or valve 25 can be used for terminating refrigerant supply.

The electronically adjustable device 115*a* may be designed only for reducing the supply bottle pressure only up to a maximal pressure difference. The maximal pressure difference may be 25 bar and more particularly 10 bar. In this situation it may be a challenge to re-open the electronically adjustable device 115*a* when the pressure in the refrigerant supply line drops below a critical value. Here a by-pass line 33*a* containing a narrow throttle 33*b* may be switched in parallel to the electronically adjustable device 115*a*. If the lumen diameter of the throttle 33*b* is smaller than 0.1 mm and more particularly smaller than 0.06 mm its flow resistance is high enough for not disturbing the operation of the electronically adjustable device 115*a* during freezing. In the standby phase between two freeze cycles the by-pass 33*a* enables a small flow parallel to the adjustment device 115*a*. Typically within 10 to 30 seconds after closing valve 21 the pressure difference across the bypass 33*a* becomes negligible. In the embodiment shown in FIG. 1*a*, a high pressure connection 33*c* of the by-pass 33*a* may be connected to a connection port of the adjustment device 115*a* which is intended for ventilating gas bubbles away from the adjustment device 115*a*. A particle filter 76*a* is foreseen for protecting the narrow lumina in adjustment device 115*a* and the high pressure path to the catheter 40 from plugging.

In the following, referring to FIG. 2, a diagram 200 showing a time (plotted along an abscissa 202) dependence of a system pressure (plotted along an ordinate 204) during operating the ablation device 1 according to an exemplary embodiment of the invention will be described.

Figure 2:
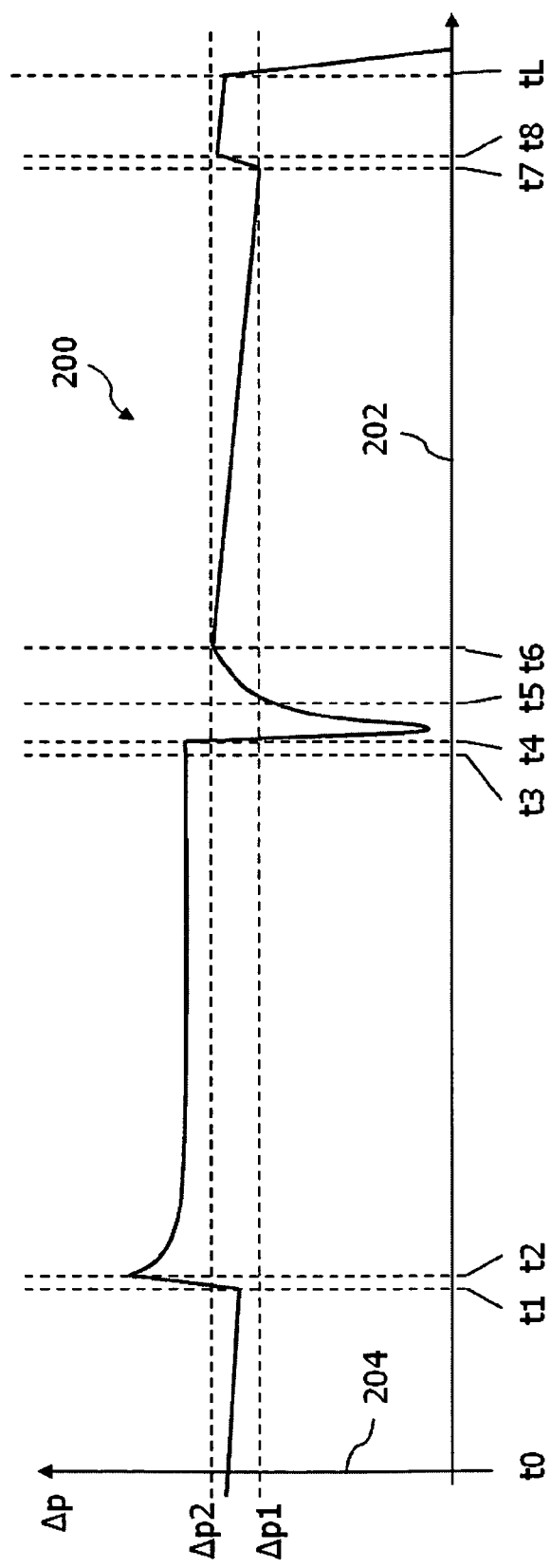
FIG. 2 illustrates a diagram showing a time dependence of a system pressure during operating an ablation device according to an exemplary embodiment of the invention.

In FIG. 2, the exhaustion pressure $\Delta p$ measured by a low pressure sensor 82 is exemplarily plotted over time t. In the depicted diagram 200, the ablation device 1 is initially (time t0) in the no-flow phase, and the exhaustion pressure is in between two predefined values $\Delta p1$ and $\Delta p2$ slowly decreasing due to residual leakage. For starting a freeze, the vacuum valve or drain valve 22 is opened at time t1, and the exhaustion pressure rises quickly due to the effect of the vacuum pump 62 and the vacuum chamber 66. Thus, the controlling system can verify the correct opening of drain valve 22 and start freezing by opening the supply valve or cooling valve 21 at time t2. During freezing (flow condition) a transient transition to an almost constant exhaustion pressure takes place. This approximately constant value is not necessarily between the limits $\Delta p1$ and $\Delta p2$.

When stopping freezing, first the cooling valve 21 is closed at t3 and the bypass valve 23 is opened at t4. The predefined time span between t3 and t4 will be kept short (typically below one second) and may even become zero. Due to the high "peak like" flow through, the exhaustion pressure sharply drops to a small value which can become also negative.

Here, it is believed that the minimum of the exhaustion pressure is determined by basically three parameters. The volume of the vacuum chamber 66 (which may be in the order of 0.5 liter to 20 liters and more particularly in the order of 1.5 to 6 liters), the mass of the refrigerant which has to be exhausted from the high pressure stream (which may be smaller than the product of the nominal catheter refrigerant mass flow rate times 30 seconds, and more particularly smaller than the nominal flow rate times 15 seconds) and the peak value of the transient flow through bypass valve 23 (which may be in the order of two to twenty times the nominal catheter flow rate). This peak flow may be adjusted by the throttle 73. The volume of the vacuum chamber 66 may be larger than the volume of the evaporated refrigerant exhausted from the high pressure stream at room temperature and more particularly larger than twice this volume. The bypass throttle 73 and the vacuum chamber 66 may be directly connected to the vacuum pump 62 (or the vacuum system of the hospital 64 if the only source is the clinic vacuum system). This avoids any peak flow across the components 22, 68, 74, 76, 82, 84 and keeps the pressure drop in the catheter back stream as small as possible.

Once the high pressure stream is emptied, the bypass line 92 is closed again at t5. The time span from t4 to t5 can be set to a predefined value. Alternatively the high pressure can be observed by pressure sensor 81, and bypass valve 23 is closed if the pressure has fallen below a threshold. Also the increase of the exhaustion pressure can be used for triggering the closing of bypass valve 23. Due to the effect of the vacuum pump 62, the exhaustion pressure increases until the upper threshold $\Delta p2$ is reached. Then the vacuum valve 22 is closed again and $\Delta p$ decreases only slowly due to the residual leakage (no-flow condition). If the lower limit $\Delta p1$ is reached again the vacuum is restored by opening (t7) and closing (t8) drain valve 22. Here the time t8–t7 can be set to a predefined value.

By closing the valves 21 and 22 the unconnected lumina are defined by the space between the closed valves 21, 22 with a well defined volume $V_0$. Assuming that the remaining gaseous refrigerant within the unconnected lumina behaves like an ideal gas at constant temperature (absolute temperature of approximately 285 K to 315 K for room temperature or body temperature) the volume of the medium sucked into the unconnected lumen is limited to the value $V_B = V_0 \times \Delta p_B / p_0$ where $p_0$ denotes the atmospheric pressure. In the worst case (with respect to hemorrhagic shock) all medium sucked into the disconnected lumen is blood. Thus, $V_B$ yields the maximal volume of blood which can be sucked in the case of a leakage. By proper technical dimensioning of the parameters (volume $V_0$, boiling chamber exhaustion pressure $\Delta p_B$) the amount of blood taken from the body in a fault condition can be limited to a desired value.

In one embodiment the low pressure part of the console may be geometrically arranged below the table on which the patient is lying (for example at an about one meter lower level). Here in case of a leakage blood might be sucked in the connection line between the console and the catheter and an additional hydrostatic pressure difference $\Delta p_H$ might be effective. In this case the volume of the medium sucked into the unconnected lumen is limited to the value $V_B = V_0 \times (\Delta p_B + \Delta p_H)/p_0$. Thus, an additional pressure may be considered when dimensioning the system. Assuming that the level of the low pressure part is about one meter below the patient and the density of blood is about 1 g/cm³ the hydrostatic pressure difference is in the order of 0.1 bar.

In the following, referring to FIG. 3, the catheter 40 including the ablation medium supply line 31 and the ablation medium drain line 32 of the ablation device 1 according to an exemplary embodiment of the invention will be described.

Figure 3:
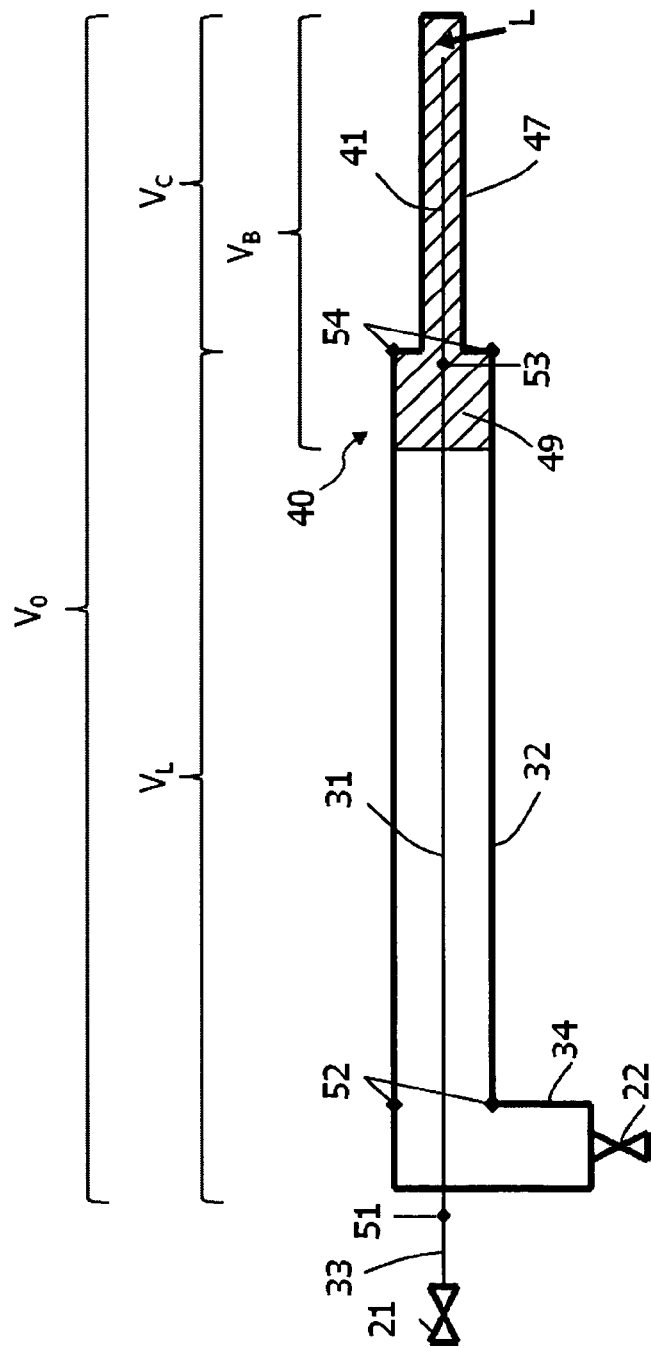
FIG. 3 illustrates a catheter including an ablation medium supply line and an ablation medium drain line of an ablation device according to an exemplary embodiment of the invention.

In FIG. 3 the volumes are schematically shown. The catheter 40 is indicated by its refrigerant supply line 41 and its outer sealing jacket 47. Connectors 53 and 54 provide a detachable connection to the connection lines for the refrigerant supply and return pathway. The volume within the catheter 40 (supply and return) defines $V_C$. The connection lines also comprise supply line 31 and an outer jacket (shown as 32) which defines the return pathway. Connectors 51 and 52 provide a detachable connection to the cryo-console. The ablation medium supply line 33 is between the connector 51 and supply valve 21. The return pathway 34 is between the connector 52 and drain valve 22. The volume between the valves 21 and 22 and the connectors 53 and 54 with the catheter 40 defines $V_L$. When the valves 21 and 22 are closed, the volumes $V_C$ and $V_L$ are not connected to the vacuum pump 62. In the case of a leakage L, blood 49 might be sucked into the catheter 40 and the connection lines (volume $V_B$, hatched area).

The volume $V_0$ is the sum of the catheter volume $V_C$ and the volume of the connection lines $V_L$. Typically $V_L$ is bigger than $V_C$, and $V_C$ is approximately in the range from 5 ml to 25 ml. In one embodiment the parameters are selected such that the volume of the sucked blood 49 $V_B$ is slightly larger than the volume of the catheter 40 $V_C$ (for example $V_B$ is 110% of $V_C$). Thus, making the connection lines in a transparent fashion the blood 49 becomes visible at the connection between the catheter 40 and the supply. As this part is continuously in the view of the operator the damage becomes immediately visible and other sources of error such as open connectors can be readily excluded. The amount of visible blood 49 is in the order of tens of milliliters which can be accepted. As a coarse indicator the volume of sucked blood 49 should not, in an embodiment, exceed 100 ml. More preferably, the sucked volume $V_B$ should be smaller than about 50 ml so that the corresponding loss of blood 49 is not dangerous for the patient.

In one embodiment the catheter handle of the catheter is made in a transparent or translucent fashion, by using a transparent or translucent material for the components defining the cover of the handle. Thus, blood becomes already visible when entering the catheter handle. In other words a smaller amount of blood sucked from the patient's body becomes visible.

The ablation device 1 may also take a defined safe state in the case of an unexpected electric power outage. Thus, in one embodiment supply valve 21 is a "normally closed" valve meaning that without the application of electric current the supply valve 21 is closed, inhibiting the delivery of the refrigerant. For disconnecting the patient from the vacuum in the case of a power outage also drain valve 22 might be a normally closed valve. Proper measures have to be taken that no high pressure occurs in the catheter 40 if drain valve 22 closed unexpectedly during freezing. Here, a pressure relief valve 74 in the low pressure part of the cryoablation system (for example in the catheter handle and/or in the cryo-console) may be used. This pressure relief valve 74 may be adapted to open if a predefined moderate over-pressure (below 0.5 bar, more particularly below 0.3 bar) occurs in the refrigerant back stream pathway. Additionally or independently a part of the controlling system may by battery powered in order to ensure a controlled shutdown in the case of a black out.

An additional supply valve 25 can be used for disconnecting the refrigerant tank 11 from the remaining cryoablation device 1. This can be used for disconnecting the catheter 40 from the refrigerant supply 11 in the case that supply valve 21 does not close at the end of the freezing cycle. Additionally the bypass valve 23 can be opened in this condition for further hampering any undesired flow to the catheter 40.

In one embodiment the bypass valve 23 is a normally open valve which is actively closed during freezing, while in another embodiment is normally closed. For avoiding that the ohmic power dissipation of additional supply valve 25 heats the refrigerant a plug valve (ball valve) can be used which is moved by an actuator (electric motor or pneumatic drive) from the closed to the open position, and vice versa.

Figure 4:
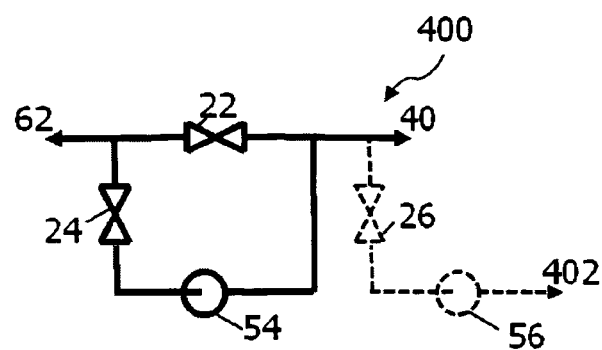
FIG. 4 illustrates an environment of a drain valve of an ablation device according to an exemplary embodiment of the invention.

In the following, referring to FIG. 4, an environment 400 of the drain valve 22 of the ablation device 1 according to an exemplary embodiment of the invention will be described.

A second vacuum valve 24 in series with a nozzle 54 is in parallel to the vacuum valve 22. Upon opening second vacuum valve 24, a small flow occurs from the catheter 40 to the vacuum pump 62 (or more generally vacuum source). This will slowly increase the exhaustion pressure $\Delta p_B$ detected by a low pressure sensor 82. By this embodiment $\Delta p_B$ can be altered any time to a desired value. Thus, in the case of a small residual leakage the preselected exhaustion pressure $\Delta p2$ can be restored at any time.

In yet another embodiment (dashed lines in FIG. 4) another valve 26 in series with another nozzle 56 provides a flow path to atmosphere 402. Opening valve 26 slowly decreases the exhaustion pressure. The valve 26 is closed when a desired value is reached. By the use of additional valves with throttles the exhaustion pressure can be kept within tight limits.

For starting freezing the vacuum valve 22 and cooling valve 21 are opened as described above. Operating the catheter 40 at constant physical parameters (for instant constant high pressure in the supply, constant temperature of the liquid refrigerant in the supply) an almost constant refrigerant flow rate will occur after a short transient initial starting phase. For defined physical parameters, this flow depends mainly on the type of catheter 40 used.

In the following, referring to FIG. 5, a boiling chamber 42 and a flow impedance 44 of a catheter 40 of the ablation device 100 according to an exemplary embodiment of the invention will be described.

Figure 5:
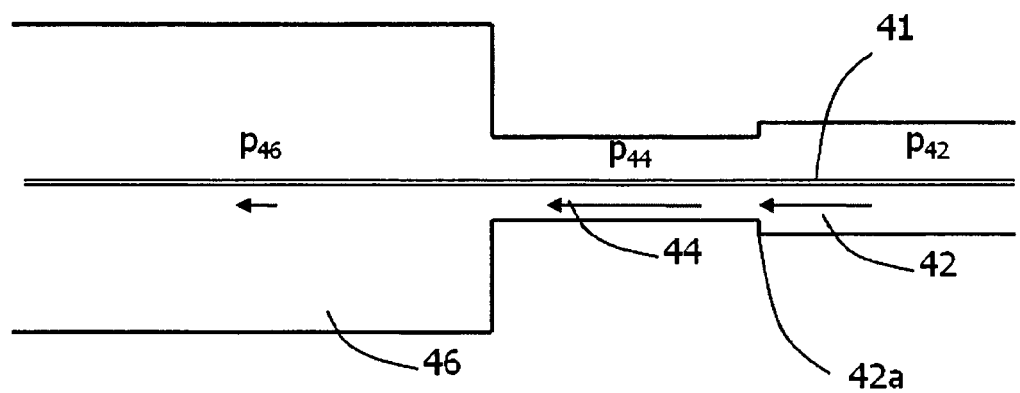
FIG. 5 illustrates a boiling chamber and a flow impedance of a catheter of an ablation device according to an exemplary embodiment of the invention.

As can be taken from FIG. 5, flow impedance 44 is selectively introduced between boiling chamber 42 and an ablation medium drain line connected to a suction chamber 46. The ablation applicator 40 comprises the boiling chamber 42 for boiling the ablation medium for ablating material from the object. The flow impedance 44 is arranged directly between the boiling chamber 42 and the suction chamber 46 of the ablation medium drain line (not shown). The ablation medium conveying unit 62 and the flow impedance 44 may be adapted so that the ablation medium has an average flow velocity in the flow impedance 44 being very close to the acoustic velocity. Around the position of the flow impedance 44, a flow may be constant and the pressure conditions (particularly the characteristic of vacuum) may vary.

In FIG. 5 a configuration is shown which reduces the influence of the exhaustion pressure in the vacuum chamber 66 $\Delta p_V$ onto the pressure in the boiling chamber 42 by taking advantage of the chocked flow phenomenon. It is assumed that the refrigerant mass flow rate m in the catheter 40 is constant and close to a known value depending on the catheter type. When designing a cryoablation catheter 40, an aim is to operate it with as little flow as needed as the flow increases the catheter dimensions. Thus, not more refrigerant is used as can boil out in the boiling chamber 42 so that basically no unused liquid refrigerant is running back the low pressure stream.

In other words, at a proximal end 42a of the boiling chamber 42 all refrigerant should be boiled into its gaseous phase. An additional structure may be foreseen for completely boiling out the refrigerant. Downstream from the boiling chamber 42 the flow path is shaped to bottleneck structure or flow impedance 44 with a cross-section only a little bit smaller than in the boiling chamber 42. Due to the mass continuity in the flow the highest flow velocity is obtained at the bottleneck 44. There are two design goals for the dimensioning of the bottleneck 44. First, for the given mass flow rate it should be narrow enough that the refrigerant flow velocity equals its theoretical maximum namely the speed of sound. Second it should be wide enough that the absolute pressure $p_{44}$ within the bottleneck 44 is slightly below the triple point pressure of the refrigerant (for example $p_{44}$ is approximately 90% of the triple point pressure).

At the proximal end of the bottleneck 44 a step-like increase to a significantly larger cross-section of suction chamber or catheter shaft 46 is desired. In other words, the designed geometry should not form a Laval nozzle like shape (the chocked flow phenomenon only occurs when supersonic flow is avoided). Due to the almost step like change of the cross-section no reaction of the shaft pressure $p_{46}$ on the sonic flow in the bottleneck 44 occurs as long as $p_{42} > p_{44}$ (chocked flow phenomenon). The pressure in the boiling chamber 42 is slightly larger than in the bottleneck 44, $p_{42} > p_{44}$. The boiling chamber 42 pressure $p_{42}$ is determined by the ratio of the cross sections in the boiling chamber 42 and the bottleneck 44 ($p_{42} = k \times p_{44}$, where k is a constant >1 depending on the cross sections). Thus, variations of the shaft pressure will not influence the boiling pressure as long as the vacuum created by the vacuum source 62 is strong enough for creating a shaft pressure $p_{46} < p_{44}$. Here the pressure sensor 82 monitors the exhaustion pressure $\Delta p$ in the console. As long this value is above a defined value, it is possible to estimate that the absolute pressure in the shaft is small enough. Additionally the refrigerant flow measured by flow sensor 84 in combination with the flow resistance of the shaft and the connection lines can be used for determining an even more accurate estimate of the shaft pressure. The term flow may denote a mass transfer per time, for example in g/s. For instance, the flow may be in a range between 0.05 g/s and 0.5 g/s (for instance for the example of nitrous oxide as a refrigerant). Optionally a miniaturized pressure transducer may be used in the shaft.

If the boiling chamber pressure is chosen only slightly above the triple point pressure the ration of the cross sections should be slightly above one. In another embodiment this ratio might equal one.

EXAMPLE

Atmospheric pressure 1000 mbar absolute

Triple point pressure $N_2O$ 878 mbar absolute choice $p_{44}$=800 mbar absolute; k=1.1→$p_{42}$=880 mbar (boiling chamber pressure absolute);

$p_{46}$<800 mbar absolute→exhaustion pressure $\Delta p_S$ is >0.2 bar.

If a leakage occurs during a freeze, the exhaustion pressure will suck blood 49 into the catheter 40. This will affect the parameters of operation (temperatures, flow rate, pressures) and the safety system will terminate the ablation. Thus, the system is brought to the zero-flow condition. The leakage will be detected by the safety system described above. Additionally, blood detectors can be used for detecting leakage during freezing. Such detectors may be build using optical sensors (the back stream is guided between an visible or infrared light source and a photosensitive detector), impedance sensors (blood is detected by an ohmic current flow between two wires), capacitive sensors (blood is detected by an increase of the capacity between to insulated wires), ultra sound sensors (blood is detected by an increase of the transmitted signal amplitude), force sensors (blood is collected in a liquid separator and weighted), etc.

In case of a leakage during icing, blood may be sucked from the patient's body into an interior lumen of the catheter 40 as a consequence of the negative pressure. This may change the operation parameters of the catheter 40 (flow, temperature, pressures). This may activate the protection system.

Upon trying to reactivate the catheter 40 again from an idle mode, the above-described leakage detection may be activated.

In the following, referring to FIG. 6, an exemplary embodiment of a precipitator 68 for the ablation device 1 will be described.

FIG. 6 shows a precipitator 68 for precipitating impurities from an ablation medium. The precipitator 68 comprises an inlet 102 adapted for being supplied with the ablation medium which may comprise impurities, an outlet 104 adapted for draining the ablation medium after at least partial removal of the potential impurities, and an impurity removal chamber 122 for at least partially removing the impurities from the ablation medium and being arranged between the inlet 102 and the outlet 104.

A floating body 114 and a sealing 118 are coupled to one another and are arranged in or at the impurity removal chamber 122. The sealing 118 is adapted for sealing the impurity removal chamber 122 in the presence of a negative pressure in the impurity removal chamber 122. The floating body 114 is adapted for being lifted within the impurity removal chamber 122 in the presence of a liquid in the impurity removal chamber 122, thereby forcing the coupled sealing 118 to allow fluid communication between an interior and an exterior of the impurity removal chamber 122.

More specifically, the precipitator 68 comprises a stud 116 coupling the floating body 114 and the sealing 118. The precipitator 68 further comprises a biasing element 120 exerting a biasing force on the floating body 116 and the sealing 118.

Liquid separator 68 provides a complementary turn-off of the vacuum in the case that a leakage occurs during the flow condition. An outer body 112 has the fluid inlet 102 and the fluid outlet 104 and is fixed to an upper plate 110 in a sealed fashion. Floating body 114 is fixed on stud 116 such that a conic (or properly shaped) upper stud portion 116a is above the plate 110 and an elongated lower portion 116b is within the body 112. A spring 120 slightly presses the upper stud 116a against a sealing 118 between the stud and the plat 110 such that the volume inside the body 112 and the plate 110 is sealed. Upon evacuation the force on the sealing increases as the pressure drops in the inner volume.

If blood is sucked during the flow condition (or even no-flow condition) the liquid is collected below the floating body 114. Note that the liquid separator 68 should be mounted with a correct vertical orientation and the gap between the floating body 114 and the wall of body 112 has to be sufficiently large. If a certain amount of blood is collected the uplift of the liquid will exceed the sum of force of the spring 120 and the force of the pressure difference between inside an outside and elevate the floating body 114. Thus, air streams into the volume decreasing the exhaustion pressure to almost zero.

If a large part of the inner volume is filled by the floating body 114, the lift force will be close to the theoretically achievable maximum and the volume which is filled by gas during normal operation becomes small. As this gas volume contributes to volume $V_L$ in FIG. 3, thus, the gas volume inside body 112 should be kept small (below 100 ml and more particularly below 20 ml) this construction is well suited for the embodiment shown in FIG. 1. The area A on which the exhaustion pressure $\Delta p$ creates a force is determined by the outer border of the sealing 118. In FIG. 6, this area is exemplarily indicated for sealing ring 118 by a hatched area. The Volume $V_F$ of the floating body 114 should be $V_F > A \Delta p/\rho + F_S$, whereas $\rho$ is the density of blood which can be approximated by the density of liquid water and $F_S$ is the force produced by the spring 120.

The surfaces in direct contact with blood may be coated by a coagulation inhibitor for avoiding clotting of the blood. When air streams into the volume within body 112 after the elevation of the stub 116a sound due to the air stream may occur providing also an acoustic signal for the error condition. A proper shape of the upper stud structure 116a may provide an easy to recognize acoustic warning.

Other embodiments of the liquid separator are possible. In one embodiment the separated liquid might be collected in a cup-like structure located within body 112. This cup like structure may act via a compensator lever on the stud 116. The stud 116 may be lifted when the weight of liquid in the cup exceeds a certain limit. The length of the lever can be used for properly trimming the forces.

In yet another embodiment the floating body 112 will close the fluid outlet 104 when lifted by the separated medium instead of acting on a stud 116.

Figure 7:
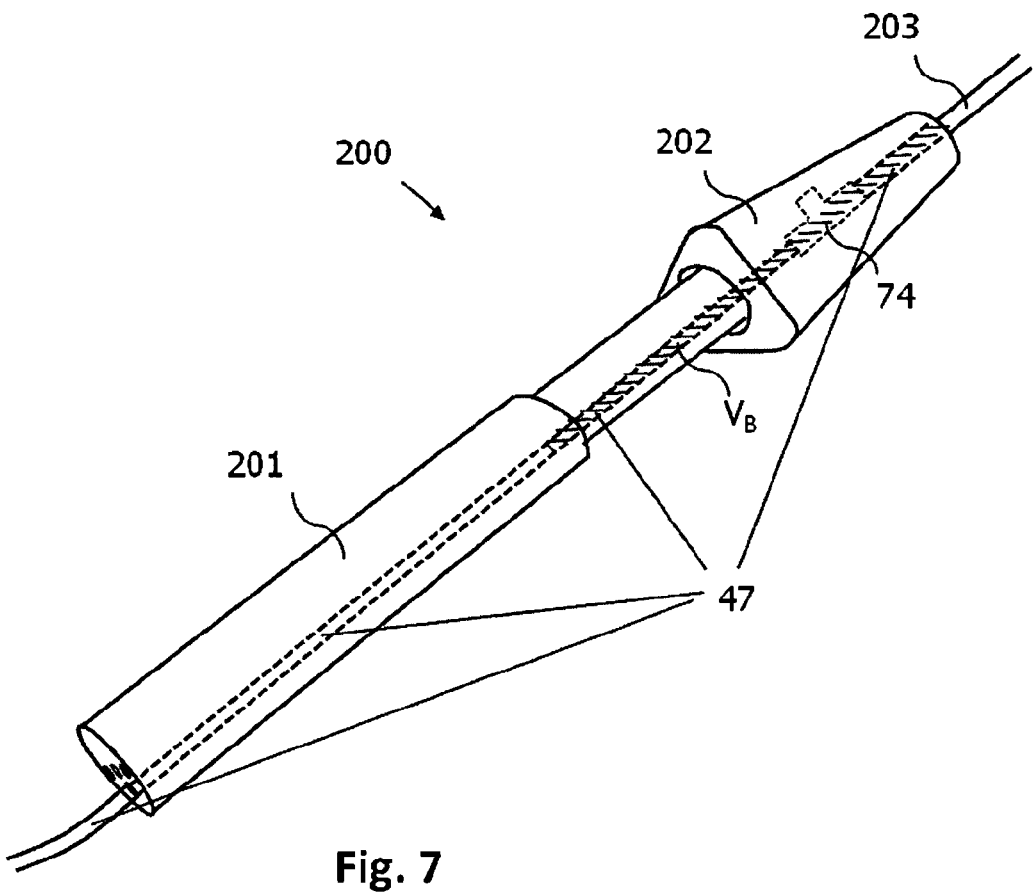
FIG. 7 illustrates a handle of an ablation device according to an exemplary embodiment of the invention.

FIG. 7 illustrates a handle 200 of an ablation device according to an exemplary embodiment of the invention.

FIG. 7 illustrates a handle 200 for handling an ablation applicator by a physician. The handle 200 comprises an optically transparent material so that blood entering the handle 200 in case of a leakage becomes quickly visible to the physician. The handle 200 may comprise or consist of a distal portion 202 and a proximal portion 201. A relative longitudinal displacement of the two handle parts 201, 202 may be translated to a manipulation of the catheter shape in the distal part such as deflection of a distal segment or formation of a geometric structure such as a loop. Here also other mechanical designs such as a sliding lever can be used for realizing a mechanical function of the handle 200. All outer enclosures of the handle 200 can be made from a transparent or translucent material such as for example polycarbonate. The catheter shaft 203 contains the refrigerant draining lumen. In the handle 200 this lumen is connected to a draining tubing 47 (sealing outer jacket of the return path). A pressure relive valve 74 may be a portion of the draining pathway. The components 47 and 74 are drawn in a hatched style, indicating that they can be seen through the transparent or translucent material of the components 201 and 202. Here the visual impression can vary for a clear view (for example in the case that the surfaces of 201 and 202 are smooth) to a kind of smeared silhouette in the case of a dimmish material (for example in the case that the surfaces of handle parts 201 and 202 are rough). It is possible that a modest coloring or staining is added to the transparent or translucent material preserving enough transparency that at least a contour of the draining pathway 47 is visible. In case of a leakage blood might be sucked into a portion of the draining lumen 47 (shaded area). Do to the transparent or translucent material of components 201 and 202 it can be visually recognized within the handle 200.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. An ablation device, comprising:
   a boiling chamber adapted for boiling an ablation medium for ablating material from an object;
   an ablation medium drain line adapted for draining the ablation medium received from the boiling chamber;
   a flow impedance arranged between the boiling chamber and the ablation medium drain line;
   an ablation medium conveying unit adapted for conveying the ablation medium to the boiling chamber, through the flow impedance and to the ablation medium drain line;
   wherein the ablation medium conveying unit and the flow impedance are adapted so that the ablation medium has an average flow velocity in the flow impedance of at least 50% of the speed of sound.

2. The ablation device according to claim 1, wherein the flow impedance is adapted as a constricted opening between the boiling chamber and a suction chamber of the ablation medium drain line via which suction chamber boiled ablation medium is sucked off.

3. The ablation device according to claim 2, wherein a cross-section of the boiling chamber is smaller than a cross-section in the suction chamber.

4. The ablation device according to claim 2, wherein a pressure in the suction chamber is smaller than a pressure in the flow impedance.

5. The ablation device according to claim 1, wherein a pressure in the boiling chamber is larger than a pressure in the flow impedance.

6. The ablation device according to claim 1 further comprising:
   an ablation applicator adapted for ablating material from an object upon delivery of the ablation medium to the ablation applicator in an ablation mode, the ablation medium drain line being adapted for draining the ablation medium received from the ablation applicator in the ablation mode;
   an ablation medium supply line adapted for supplying the ablation medium to the ablation applicator in the ablation mode; and
   a closure mechanism adapted for selectively enclosing a predefined volume in a fluidic path upon operating the ablation device in a no-flow mode or upon detecting a leak in the fluidic path, the fluidic path including the ablation applicator and being defined between the ablation medium supply line and the ablation medium drain line.

7. The ablation device according to claim 1, wherein the boiling chamber and an amount of ablation medium used are adapted such that at a proximal end of the boiling chamber all ablation medium is boiled into its gaseous phase.

8. The ablation device according to claim 1, the ablation medium is nitrous oxide.

9. The ablation device according to claim 2, wherein at the proximal end of the flow impedance there is a step-like increase to a significantly larger cross-section of the suction chamber.

10. The ablation device according to claim 1, wherein the boiling chamber pressure is chosen above a triple point pressure of the ablation medium.

11. The ablation device according to claim 1, further comprising:
    a flow sensor measuring a flow of the ablation medium.

12. The ablation device according to claim 1, further comprising:
    a pressure sensor monitoring a difference of pressure between a surrounding medium and a vacuum in an ablation medium line.

13. The ablation device according to claim 1, further comprising:
    a miniaturized pressure transducer in the suction chamber.

14. The ablation device according to claim 1, further comprising:
    a leakage detector for detecting a leakage during freezing.

15. The ablation device according to claim 14, wherein the leakage detector is one of a blood sensor, a pressure sensor, a flow sensor or a boiling temperature sensor.

16. The ablation device according to claim 1, wherein the boiling chamber pressure is larger than 878 mbar absolute.

17. The ablation device according to claim 1, wherein a flow rate of the ablation medium is in a range between 0.05 g/s and 0.5 g/s.

18. An ablation method, comprising:
    conveying an ablation medium to a boiling chamber from a conveying unit through a flow impedance and to an ablation medium drain line;
    boiling the ablation medium in the boiling chamber for ablating material from an object;
    draining the ablation medium received from the boiling chamber in the ablation medium drain line;
    impeding the flow with the flow impedance arranged between the boiling chamber and the ablation medium drain line; and
    conveying the ablation medium with an average flow velocity of at least 50% of the speed of sound to the boiling chamber, through the flow impedance and to the ablation medium drain line through the flow impedance.

19. The method according to claim 18, wherein the ablation medium is conveyed with a flow rate in a range between 0.05 g/s and 0.5 g/s.

20. The method of claim 18, wherein the ablation medium is nitrous oxide and the boiling chamber pressure is larger than 878 mbar absolute.

* * * * *